(12) United States Patent
Uchida (10) Patent No.: US 7,598,483 B2
(45) Date of Patent: Oct. 6, 2009

(54) OPTICAL ELEMENT AND OPTICAL MEASUREMENT DEVICE USING THE OPTICAL ELEMENT

(75) Inventor: Shinji Uchida, Osaka (JP)

(73) Assignee: Panasonic Corporation, Osaka (JP)

( * ) Notice: Subject to any disclaimer, the term of this patent is extended or adjusted under 35 U.S.C. 154(b) by 364 days.

(21) Appl. No.: 11/547,164

(22) PCT Filed: Feb. 1, 2006

(86) PCT No.: PCT/JP2006/301686

§ 371 (c)(1),
(2), (4) Date: Oct. 2, 2006

(87) PCT Pub. No.: WO2006/082859

PCT Pub. Date: Aug. 10, 2006

(65) Prior Publication Data

US 2008/0265145 A1    Oct. 30, 2008

(30) Foreign Application Priority Data

Feb. 2, 2005 (JP) .............................. 2005-026576
Feb. 10, 2005 (JP) .............................. 2005-034988

(51) Int. Cl.
*H01J 3/14* (2006.01)
(52) U.S. Cl. ...................... 250/216; 250/556; 382/124; 600/310
(58) Field of Classification Search ................. 250/216, 250/555, 556; 382/115, 124; 356/432; 600/310
See application file for complete search history.

(56) References Cited

U.S. PATENT DOCUMENTS 4,534,651 A     8/1985    Minikane (Continued)

FOREIGN PATENT DOCUMENTS

CN     1122911 A     5/1996

(Continued)

OTHER PUBLICATIONS

Chinese Office Action, with English Translation, issued in Chinese Patent Application CN 2006-80000139 dated on Dec. 26, 2008.

(Continued)

*Primary Examiner*—Georgia Y Epps
*Assistant Examiner*—Kevin Wyatt
(74) *Attorney, Agent, or Firm*—McDermott Will & Emery LLP (57) ABSTRACT

Provided is an optical element in which a groove for a sample to make contact can be formed without machining or etching a material for an optical element, and in which the scattering of a light at the groove does not decrease the precision in an optical measurement. The optical element is formed with a light-emitting prism including a light-output face from which a light to be emitted to a sample is outputted, a light-receiving prism including a light-receiving face which receives the light returned from the sample, and a light intensity-reducing part provided between the light-emitting prism and the light-receiving prism. The light-emitting prism and the light-receiving prism are combined to form a recessed part for the sample to make contact, so that the light outputted from the light-output face travels straight in the sample in contact with the recessed part and enters the light-receiving face.

3 Claims, 4 Drawing Sheets

U.S. PATENT DOCUMENTS

| | | | |
|---|---|---|---|
| 4,702,557 A * | 10/1987 | Beckmann et al. | 349/197 |
| 4,969,730 A * | 11/1990 | van den Brandt | 353/31 |
| 5,107,327 A * | 4/1992 | Nishimori et al. | 257/793 |
| 5,125,740 A * | 6/1992 | Sato et al. | 356/128 |
| 6,091,438 A * | 7/2000 | Endo | 347/221 |
| 6,898,027 B2 | 5/2005 | Yamada et al. | |
| 7,064,906 B2 | 6/2006 | Yamada et al. | |
| 2002/0123677 A1 | 9/2002 | Miki et al. | |
| 2003/0109030 A1* | 6/2003 | Uchida et al. | 435/287.1 |
| 2003/0123063 A1* | 7/2003 | Mukai et al. | 356/445 |
| 2004/0075915 A1 | 4/2004 | Yamada et al. | |
| 2004/0145731 A1* | 7/2004 | Nakajima et al. | 356/135 |
| 2004/0190826 A1* | 9/2004 | Ghiron et al. | 385/36 |
| 2005/0146800 A1 | 7/2005 | Yamada et al. | |
| 2006/0001884 A1* | 1/2006 | Tani et al. | 356/445 |
| 2006/0041195 A1* | 2/2006 | Shioi et al. | 600/310 |

FOREIGN PATENT DOCUMENTS

| | | |
|---|---|---|
| CN | 1502049 | 12/2008 |
| EP | 1 464 273 A | 10/2004 |
| JP | 60-111946 | 8/1985 |
| JP | 62-079332 | 4/1987 |
| JP | 63-14143 | 1/1988 |
| JP | 01-197632 | 8/1989 |
| JP | 2002-202258 | 7/2002 |
| JP | 2002-214135 | 7/2002 |
| JP | 2004-290226 | 10/2004 |
| WO | WO 88/02109 | 3/1988 |
| WO | WO 01/58355 A1 | 8/2001 |

OTHER PUBLICATIONS

Zhang et al., "Violet light generation by frequency doubling of GaAlAs diode laser using a metallo-organic complex crystal ZnCd(SCN)4," Optics & Laser Technology, Elsevier Science Publishers BV., Amsterdam, NL, vol. 33, No. 2, Mar. 1, 2001, pp. 121-124, XP004316882.

European Search Report issued in European Patent Application No. EP 06712829.8 dated May 29, 2009.

* cited by examiner

OPTICAL ELEMENT AND OPTICAL MEASUREMENT DEVICE USING THE OPTICAL ELEMENT

RELATED APPLICATION

This application is a national phase of PCT/JP2006/301686 filed on Feb. 1, 2006, which claims priority from Japanese Application Nos. JP 2005-026576 filed Feb. 2, 2005 and JP 2005-034988 filed Feb. 10, 2005, the disclosures of which Applications are incorporated by reference herein. The benefit of the filing and priority dates of the International and Japanese Applications is respectfully requested.

TECHNICAL FIELD

The present invention relates to optical elements and optical measurement devices using the optical elements used for measuring a concentration of glucose, cholesterol, urea, triglyceride, or the like in a sample by optically measuring a sample of a living body tissue, a solution, or the like.

BACKGROUND ART

There have been proposed so far various optical elements and optical measurement devices used for measuring a specific component in a living body tissue or a solution. For example, International Publication No. 01/58355 A1 has proposed a method for obtaining information on inside living body by bringing a living body tissue into contact with an optical element having grooves and using the difference in refractive indexes between the grooves and the living body tissue.

Figure 8:
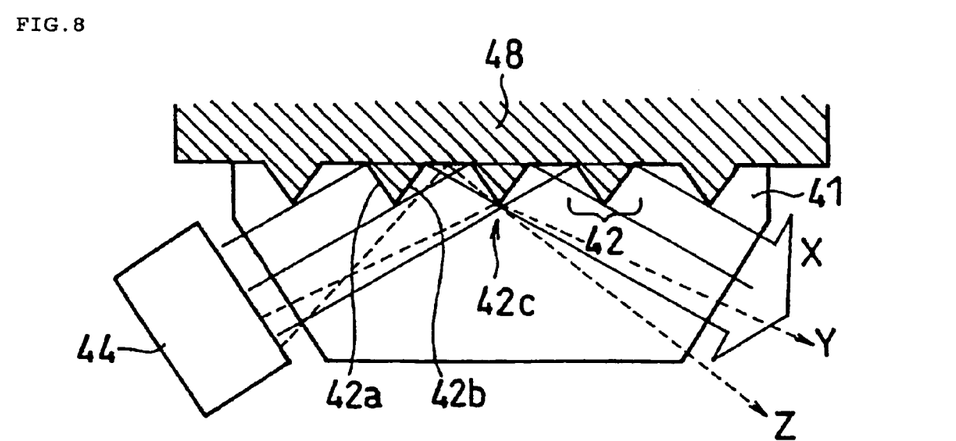
[FIG. 8] A structural diagram of a conventional optical element having grooves contacting the sample.

FIG. 8 is a structural diagram of a conventional optical element having grooves as proposed in International Publication No. 01/58355 A1. The arrows in FIG. 8 show paths of the light outputted from the light source 44. The light (arrow X in FIG. 8) entered into the side faces 42a of the grooves 42 in the optical element 41 is outputted from the side faces 42b, after passing through the living body tissue 48. Information on the living body tissue can be obtained by detecting the outputted light with a detector or the like.

DISCLOSURE OF INVENTION

Problems to be Solved by the Invention

Such grooves 42 in the conventional optical element as in the above are directly formed on a plane of a material for optical elements, mainly by machining such as surface grinding or ultrasonic machining, or by etching. However, these methods have problems in that the obtained grooves 42 are easily damaged and a smoothly worked surface is hardly obtained, in addition to a difficulty in processing into specific forms.

For example, in the case of grooves 42 shown in FIG. 8, a grindstone with a V-shaped processing face is rotated and pressed against the plane of a material for optical elements, so as to form the letter V shape. In this method, the precision in the grindstone shape is directly reflected on the precision in the processing and on the surface roughness. Thus, when the grindstone is worn out, the depth and shape of the grooves 42 change, and the surface roughness is increased, making the processing of the grooves 42 into a certain shape with precision difficult. Additionally, when the depth and shape of the grooves 42 are changed and the surface roughness of the processed surface is increased, the actual light path may differ from the designed path, or the light may scatter at the surface of the grooves 42, leading to a decreased measurement precision.

Further, the light emitted from the light source 44 is generally a directional light, though not perfectly directional. Thus, unnecessary lights, such as a light reflected at the bottom 42c of the grooves 42 (arrow Y in FIG. 8), a light reflected at a face other than the grooves 42 (arrow Z in FIG. 8), and a light reflected at the entrance plane 42a and the inside of the optical element 42 without entering the living body tissue 48 and then outputted (not shown), are detected with the above light X, reducing the measurement precision.

Thus, in view of the above conventional problems, the present invention aims to provide an optical element that can be formed easily and is excellent in measurement precision, and also a highly reliable optical measurement device using the optical element, with easy and simple method.

Means for Solving the Problem

An optical element of the present invention comprises:
a light-emitting prism including a light-output face from which a light to be emitted to a sample is outputted;
a light-receiving prism including a light-receiving face which receives the light returned from the sample; and
a light intensity-reducing part provided between the light-emitting prism and the light-receiving prism;
wherein the light-emitting prism and the light-receiving prism are combined to form a recessed part with which the sample makes contact; and
a light outputted from the light-output face enters the light-receiving face by traveling straight in the sample in contact with the recessed part.

The "light intensity-reducing part" in the present invention refers to a member or a part with a function of reducing the amount of passing light. Additionally, the "light-reducing" in present invention means reducing the amount of light outputted relative to the amount of light entered when the light travels between two or more mediums, i.e., reducing the amount of passing light. For example, it includes (i) reducing the amount of passing light by changing a refractive index (reflectivity) between the mediums, and (ii) reducing the amount of passing light by blocking the light (for example, reflecting and absorbing).

An optical measurement device of the present invention comprises;
the above optical element of the present invention;
a light source for outputting a light to the light-emitting prism to emit the light to the sample from the light-emitting prism; and
a photodetector for detecting the light returned to the light-receiving prism from the sample.

Effects of the Invention

Based on the present invention, an optical element with recessed part can be formed easily, and an optical element in which decrease in measurement precision caused by unnecessary lights such as reflected light inside the optical element is suppressed can be obtained. Additionally, by using the optical element of the present invention, a highly reliable optical measurement device can be realized easily and simply.

BEST MODE FOR CARRYING OUT THE INVENTION

An optical element of the present invention comprises: a light-emitting prism including a light-output face from which a light to be emitted to a sample is outputted; a light-receiving prism including a light-receiving face which receives the light returned from the sample; and a light intensity-reducing part provided between the light-emitting prism and the light-receiving prism;

characterized in that the light-emitting prism and the light-receiving prism are combined to form a recessed part with which the sample makes contact, and the light outputted from the light-output face enters the light-receiving face by traveling straight in the sample in contact with the recessed part.

Based on such structure, the amount of light entering the light-receiving prism from the lights passing through the light-emitting prism but not passing through the sample can be decreased. That is, from the light that passed through the light-emitting prism, the amount of light that enters the light-receiving prism without passing through the sample can be reduced. Then, arrival of unnecessary light to a photodetector to be mentioned later can be suppressed, and decline in measurement precision can be reliably suppressed.

Additionally, since each face of the light-emitting prism and the light-receiving prism forming the recessed part is processed and then the light-emitting prism and the light-receiving prism are combined to form the recessed part, a smoothing process of the surface of the recessed part after forming the recessed part is unnecessary. Thus, a smooth-surfaced recessed part can be formed easily, and an optical element without a decline in optical measurement precision due to scattered light at the recessed part can be obtained.

The above recessed part can be easily formed by for example combining a planar processed face. Other than that, known techniques are used to form the above recessed part with a composite plane such as a staircase form formed with a plurality of planes. The above recessed part can be formed as well by combining curved faces.

Also, since the above recessed part is formed by processing the light-emitting prism and the light-receiving prism to give a predetermined form and then combining these prisms, particularly, the bottom part of the recessed part is processed with ease and precision.

The light intensity-reducing part may be a gap provided between the light-emitting prism and the light-receiving prism.

Based on such structure, since the difference in the refractive indexes of the light-emitting prism and the light-receiving prism and the refractive index of the gap causes a reflected light to be generated at their respective interfaces, the amount of light entering the light-receiving prism without passing through the sample can be reduced from the light which passed through the light-emitting prism. Then, arrival of unnecessary light to the photodetector to be mentioned later can be suppressed, and decline in measurement precision can be reliably suppressed.

Also, the light intensity-reducing part may be a light-blocking part provided between the light-emitting prism and the light-receiving prism.

Based on such structure, the light-blocking part provided between the light-emitting prism and the light-receiving prism can block the light entering the light-receiving prism without passing the sample, among the light which passed through the light-emitting prism. Also, arrival of unnecessary light to the photodetector to be mentioned later can be suppressed, and decline in measurement precision can be reliably suppressed.

Further, the optical element of the present invention preferably includes a spacer provided between the light-emitting prism and the light-receiving prism.

Based on such structure, by changing the thickness of the spacer to change the distance between the light-emitting prism and the light-receiving prism, the measurement position in the depth direction of the sample can be easily adjusted. When the distance between the light-emitting prism and the light-receiving prism is widened, the sample goes deeper into the recessed part with which the sample is in contact, and as a result, a deep portion of the sample can be measured. On the other hand, when the distance between the light-emitting prism and the light-receiving prism is narrowed, the sample does not easily goes into the recessed part, and as a result, a surface portion of the sample can be measured.

The spacer can be formed with the material same as that of the above light intensity-reducing part. For example, when the spacer is formed with the material having a lower refractive index than that of the light-emitting prism and the light-receiving prism, the spacer can be provided with a role same as that of the above light intensity-reducing part.

It is preferable that the light-output face of the light-emitting prism is a first slope part which is planar and is for the sample to make contact, and the light-receiving face of the light-receiving prism is a second slope part which is planar and is for the sample to make contact: the first slope part and the second slope part face to form the recessed part, and a cross section of the recessed part in the direction vertical to the first slope part and the second slope part thereof has roughly a shape of letter-V.

Based on such structure, since the first slope part and the second slope part are individually subjected to optical grinding and then the first slope part and the second slope part are faced to form the recessed part in letter-V shape for the sample to make contact, a recessed part with a higher optical precision and smooth plane can be obtained easily. Additionally, when the recessed part has a letter-V shape, the sample easily stay and the optical path length can be made stable.

Further, the optical element of the present invention preferably includes a cover forming a sample-holding part by covering a part of the recessed part and by being combined together with the light-emitting prism and the light-receiving prism. Such cover may be formed for example with a first cover and a second cover disposed to cover a side of the light-emitting prism, a side of the light-receiving prism, opening a top face of the recessed part.

Based on such structure, since the sides of the recessed part are enclosed with the light-emitting prism, the light-receiving prism, and the cover, even when the sample is in liquid form, the sample can be held in the recessed part functioning as a sample-holding part without being spilled.

Further, the optical element of the present invention preferably includes an adjusting means for adjusting the distance between the light-emitting prism and the light-receiving prism.

Based on such structure, the distance between the light-emitting prism and the light-receiving prism can be changed further easily and simply, and the measurement position in the depth direction of the sample can be adjusted easily and simply. When the distance between the light-emitting prism and the light-receiving prism is widened, the sample in contact with the recessed part goes into the recessed part further deeply, and as a result, a deeper part of the sample can be measured. On the other hand, when the distance between the light-emitting prism and the light-receiving prism is narrowed, the sample does not easily go into the recessed part, and as a result, the surface part of the sample can be measured.

The optical measurement device of the present invention is characterized by comprising: the above optical element of the present invention; a light source for outputting a light to the light-emitting prism for emitting the light from the light-emitting prism to the sample; and a photodetector for detecting the light returned from the sample to the light-receiving prism.

Since such structure uses the above optical element of the present invention, a highly reliable optical measurement device can be provided with an easy and simple method.

The optical measurement device of the present invention preferably comprises a spectroscopic element disposed between the light-receiving prism and the photodetector.

Based on such structure, only the light necessary for the measurement can be sent to the photodetector further reliably, and an improvement in measurement precision can be realized.

In the following, representative embodiments of the present invention are described in detail with reference to the drawings. In the following description, same reference numerals are used for the same or corresponding part, and redundant description may be omitted.

The embodiments described below illustrate examples of the present invention, and the present invention is not limited thereto.

Embodiment 1

Figure 1:
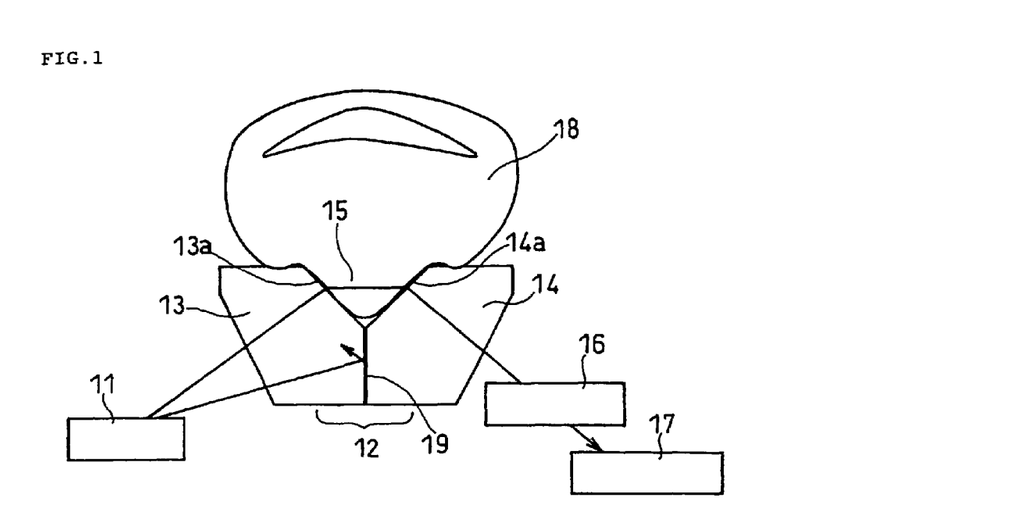
[FIG. 1] A diagram showing a structure of an optical measurement device in Embodiment 1 of the present invention.

FIG. 1 is a diagram showing a structure of an optical measurement device (a measurement device for a concentration of a component) using an optical element (measurement element) of the present invention in Embodiment 1 of the present invention, and the arrows in the diagram show light paths. In the following, the optical element is described first.

As shown in FIG. 1, an optical element 12 is formed by combining and integrating a light-emitting prism 13 for emitting a light to a sample and a light-receiving prism 14 for receiving the light returned from the sample, and a recessed part 15 for a sample to make contact is formed between the light-emitting prism 13 and the light-receiving prism 14. Also, in this embodiment, as a light intensity-reducing part 19, a light-blocking part is formed between the light-emitting prism 13 and the light-receiving prism 14, to block the light between the prisms.

The recessed part 15 is formed by grinding a first slope part 13a to which the sample makes contact in the light-emitting prism 13 and a second slope part 14a to which the sample makes contact in the light-receiving prism 14 to give smooth faces, and then by joining the light-emitting prism 13 and the light-receiving prism 14 so that the first slope part 13a and the second slope part 14a face each other to form a letter-V shape.

Since each of the first slope part 13a and the second slope part 14a that are planar is optically ground before joining the light-emitting prism 13 and the light-receiving prism 14, the first slope part 13a and the second slope part 14a can be smoothed easily. From those reason, the recessed part 15 with faces having higher optical precision can be obtained easily.

Additionally, since the optical element 12 in this embodiment can be disassembled into the light-emitting prism 13 and the light-receiving prism 14, the recessed part can be easily cleaned, compared with conventional optical elements (ref. FIG. 8) that cannot be disassembled.

For the material forming the light-emitting prism 13 and the light-receiving prism 14, known ones in the art can be used.

When substances with the absorption peak in the mid-infrared region are to be measured, silicon, germanium, SiC, diamond, ZnSe, ZnS, or KrS may be used, for example.

As in glucose having the absorption peak at 1033 $cm^{-1}$ and 1080 $cm^{-1}$ in wavenumber, when a substance having the absorption peak in the mid-infrared region is to be measured, silicon or germanium is used preferably, in view of a higher transmittance for infrared wavelength of about 9 to 10 microns, and higher workability and mechanical strength.

When a substance with the absorption peak in the near-infrared region is to be measured, molten quartz, monocrystal silicon, optical glass, or transparent resin may be used.

The light intensity-reducing part 19 in this embodiment is for example a light-blocking part in film-form, sheet-form, plate-form, or rod-form, and has a function of preventing the light that does not reach the recessed part, i.e. the light that does not pass through the sample, from entering the light-receiving prism, among the light that passed through the light-emitting prism.

For the light-blocking part, a metal reflective film of Al, Cu, or Ag, an absorption film of Cr or a black ink, or a dielectric multilayer is used preferably. A multilayer formed of a metal layer and a dielectric layer may be used as well. For the film forming method for the light-blocking part in such cases, known methods such as vacuum deposition, sputtering, or CVD method may be used. Also, a film may be formed directly on the surface of the light-emitting prism 13 or the light-receiving prism 14; or a film may be formed on their respective prisms, and then each of the films may be joined together.

For the above light-blocking part, other than the sheet formed of the above material for the film, for example, an aluminum foil or a Cu metal sheet may be used. A metal sheet may be affixed on the light-emitting prism 13 or on the light-receiving prism 14 directly; or a metal sheet may be formed on respective prisms, and then each of the sheets may be joined together.

Further, for the above light-blocking part, a plate formed of the material of the above film or the above sheet may be used.

An optical measurement device in this embodiment can be obtained by using the optical element 12 in this embodiment with the above form. The optical measurement device in this embodiment comprises: the optical element 12; a light source 11 for outputting a light; spectroscopic element 16 for separating the light returned from the sample via the light-receiving prism 14; and a photodetector 17 for detecting the light that passed through the spectroscopic element 16. By using the above optical element 12 with a higher optical precision, the measurement precision improves and a higher reliability can be obtained.

Additionally, since the light intensity-reducing part 19 prevents the light not passing the sample from entering the light-receiving prism as in the above, the light reflected by the face forming the recessed part without passing the sample, and unnecessary light from the light source do not arrive at the photodetector 17. Thus, the S/N ratio of the optical measurement device improves.

For the light source 11, any one can be used without particular limitation, as long as the light includes the absorption wavelength of the component to be measured.

For example, in the case of the light of the mid-infrared region, a Globar light source in which SiC is sintered into a rod-like form, $CO_2$ laser, a tungsten lamp, an infrared pulse light source, or a QCL light source may be used.

When a substance having an intense absorption peak in the mid-infrared region, such as glucose, is to be measured, for example, a Globar light source, infrared pulse light source, or a QCL light source is preferable.

When a substance having the absorption peak in the near-infrared region is to be measured, for example, a halogen light source, a semiconductor laser, or LED may be used. Glucose is known to have the absorption peak in the near-infrared region, in addition to the mid-infrared region. For example, a DFB laser or a DBR laser for LED light communication is preferably used.

For the spectroscopic element 16, for example, a grating element or an optical filter element may be used. FT-IR, laser spectrometer, or the like may be used as well. The position of the spectroscopic element is not particularly limited.

For the photodetector 17, known ones in the art can be used. For example, in the mid-infrared region, a pyroelectric sensor, a thermopile, a thermistor, or an MCT detector (a HgCdTe detector which is a kind of a quantum detector) may be used. In the near-infrared region, for example, InGaAs detector, photodiode, PbS detector, InSb detector, InAs detector, or a sensor array of these detectors may be used.

A measurement method of a component concentration by using the optical measurement device of the present invention as in the above is described next. A case described here is a measurement for a finger as a living body tissue.

First of all, a finger 18 is pressed against to abut the recessed part 15 of the optical element 12. At this time, just by pressing the finger lightly against the recessed part, as shown in FIG. 1, the finger 18 goes into the recessed part 15. Next, when a light is emitted to the part of the finger 18 that went into the recess, the light outputted from the light source 11 reaches the light-emitting prism 13 of the optical element 12, and the light reached the light-emitting prism 13 reaches the recessed part 15 or the light-blocking part 19 provided at the optical element 12.

Then, the light that reached the light intensity-reducing part 19 is absorbed or reflected, not to enter the light-receiving prism 14. The light reached the recessed part 15, upon being outputted from the recessed part 15, is refracted by the difference in refractive indexes of the light-emitting prism 13 and the finger 18, and passes through the finger 18.

On the other hand, the light that passed through the finger 18 enters the light-receiving prism 14. Since the light goes through such path as in the above, the light-receiving prism 14 can easily receive a large amount of the light that travels straight in the finger 18 and the light passed through the light-receiving prism 14 reaches the photodetector 17 via the spectroscopic element 16. Based on the light detected by the photodetector 17, for example, parameters of a living body tissue such as a glucose concentration can be calculated.

Although the distance that the light passes through in the finger 18 is not particularly limited, the distance may be set to about 1 to 2 mm, for example. Additionally, in the recessed part 15, an angle formed between the first slope part and the second slope part is not limited particularly, and may be set to for example, 90 degrees.

The entrance angle of the light to the finger 18, the sample, is determined by the shape of the recessed part 15, and the refractive indexes of the light-emitting prism 13 and the light-receiving prism 14. The refractive indexes of the light-emitting prism 13 and the light-receiving prism 14 are preferably larger than the refractive index of the sample. Upon measurement, since it is preferable to bring the light that passed through the sample to the photodetector 17 as much as possible, the shape of the recessed part 15 and the entrance angle of the light relative to the finger 18 are preferably set according to the refractive index of the sample, in addition to the refractive index of the optical element 12.

The spectroscopic element 16 can pass through only the light necessary for detecting the concentration of the component, for example. The concentration of the component is calculated based on the light detected by the photodetector 17. That is, a light with a specific wavelength is absorbed according to the component and reduced, and since the reduction amount of the light is dependent upon the concentration of the component, the concentration of the component is calculated from the reduced amount of the light.

Figure 2:
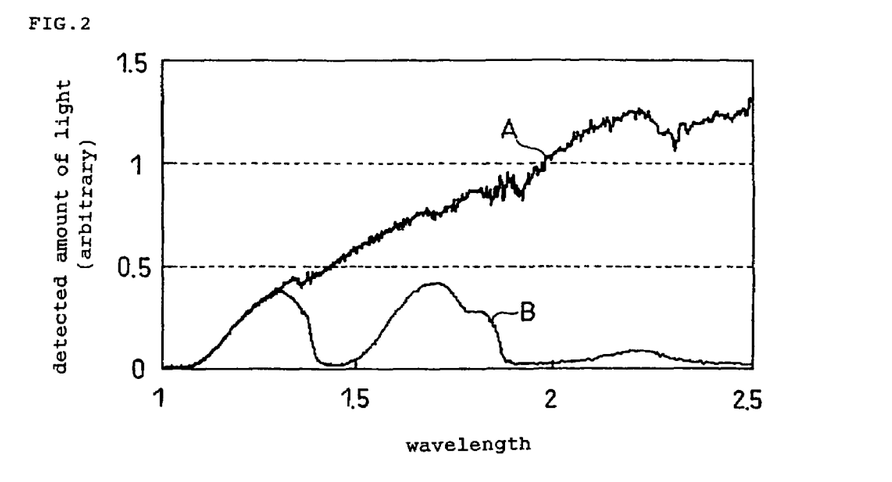
[FIG. 2] A characteristic diagram showing wavelength characteristics of the transmitted and detected light amount when the transmitted and detected light amount of a finger is measured by using the optical measurement device in FIG. 1.

An example of the results of the measurement on the finger 18 as a living body tissue by using the above optical measurement device of the present invention is shown in FIG. 2. The horizontal axis shows wavelength, and the vertical axis shows the detected amount of light in arbitrary values. "A" shows the measurement results before the finger 18 is pressed against the recessed part, and "B" shows measurement results when the finger 18 is pressed against the recessed part.

These results show that the spectle changes greatly when the finger 18 is pressed against the recessed part, relative to the spectle before the finger 18 is pressed against the recessed part. This is probably because the light from the light source 11 is greatly absorbed and reduced, due to blood components such as water, glucose, neutral fat, and cholesterol in the finger 18 and also various components forming the finger 18. For example, the light is greatly reduced at 1.4 microns. This corresponds to the absorption spectrum of water, which shows the existence of water in the living body.

Figure 3:
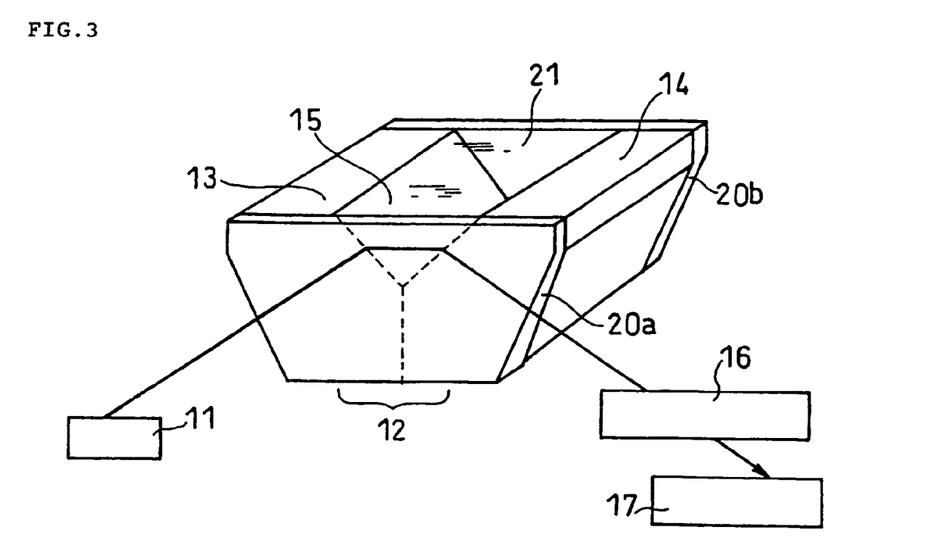
[FIG. 3] A diagram showing a structure of a modified version of an optical measurement device in Embodiment 1 of the present invention.

FIG. 3 shows a diagram showing a structure of a modified version of an optical measurement device of this embodiment. This modified version is for measuring the concentration of the component in a sample liquid such as a solution or a liquid, and the optical element 12 further comprises a first measurement cover 20a and a second measurement cover 20b, in addition to the light source 11, the optical element 12, the light-emitting prism 13, the light-receiving prism 14, the recessed part 15, the spectroscopic element 16, and the photodetector 17 as in FIG. 1.

The first measurement cover 20a and the second measurement cover 20b cover the light-emitting prism 13 and the light-receiving prism 14, while leaving the top part of the recessed part 15 open.

That is, the recessed part 15 is surrounded by the first slope part 13a, the second slope part 14a, the first measurement cover 20a, and the second measurement cover 20b, to function as a sample-holding part for holding a sample liquid 21. Thus, the sample liquid 21 can be held in the recessed part 15, without being spilled over.

Based on such form, in this modified version, just by adding the measurement covers to the form in FIG. 1, the component in the sample liquid can be measured easily.

Embodiment 2

Figure 4:
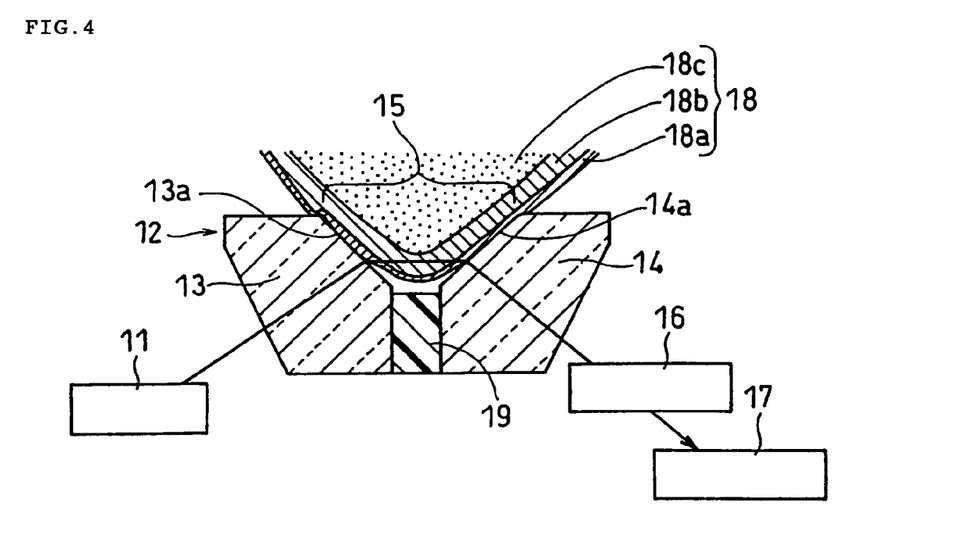
[FIG. 4] A diagram showing a structure of an optical measurement device in Embodiment 2 of the present invention.

FIG. 4 is a diagram showing a structure of an optical measurement device (a measurement device for a concentration of a component) in Embodiment 2 of the present invention, using the optical element of the present invention (measurement element), and the arrow in the figure shows a light path. In the following, an optical element is described first.

As shown in FIG. 4, an optical element 12 is formed by combining to integrate a light-emitting prism 13 for emitting a light on a sample and a light-receiving prism 14 for receiving the light returned from the sample. Between the light-emitting prism 13 and the light-receiving prism 14, formed is a recessed part 15 having roughly a letter-V shape to which the sample makes contact. In this embodiment, a light intensity-reducing part 19 is provided, for reducing the amount of light entering the light-receiving prism 14, from the light that passed through the light-emitting prism 13 but did not pass through the sample between the light-emitting prism 13 and the light-receiving prism 14, while regulating the distance between the light-emitting prism 13 and the light-receiving prism 14.

The light intensity-reducing part 19 is formed by a material with a smaller refractive index (for example, glass or plastics) than the refractive indexes of the light-emitting prism 13 and the light-receiving prism 14, and has function of reducing the amount of light entering the light-receiving prism 14 from the light that passed through the light-emitting prism 13 but did not pass through the sample due to changes in the refractive index (i.e., reflectance).

Although the thickness (width) of the light intensity-reducing part 19, that is, the distance between the light-emitting prism 13 and the light-receiving prism 14, is not particularly limited, the distance is preferably 3 mm or less when for example a living body tissue is to be measured, since an excessively long optical path length causes a large absorption by water.

In this embodiment, the light intensity-reducing part 19 has a rectangular shape, and the recessed part 15 is formed to have roughly a shape of letter V by a combination of the light-emitting prism 13, the light-receiving prism 14, and the light intensity-reducing part 19. Also, the first slope part 13a which is planar and to which the sample makes contact in the light-emitting prism 13, and the second slope part 14a which is planar and to which the sample makes contact in the light-receiving prism 14 are deposed to face each other, and form side faces of the recessed part 15. The top face of the light intensity-reducing part 19 is positioned between the lower end of the first slope part 13a and the lower end of the second slope part 14a to form the bottom face of the recessed part 15.

Therefore, by changing the thickness (width) of the light intensity-reducing part 19, the light path of the light that passes through the recessed part 15 can be changed easily. That is, when the light intensity-reducing part 19 is to be made thicker, the distance between the light-emitting prism 13 and the light-receiving prism 14 increases, the living body goes deeper into the recessed part 15, and a further deeper part of the living body can be measured. Also, when the light intensity-reducing part 19 is made thinner, the distance between the light-emitting prism 13 and the light-receiving prism 14 decreases, and a further outer layer of the living body can be measured. By thus providing the light intensity-reducing part 19 with the function as a spacer and appropriately setting the thickness of the light intensity-reducing part 19, the living body can be measured at a desired depth.

The tissues of the finger 18 include epidermis 18a, an outermost surface, dermis 18b below the epidermis, and subcutaneous fat 18c. When a glucose concentration for example is to be measured, the dermis 18b between the epidermis 18a and the subcutaneous fat 18c is preferably measured, and it is preferable that a large amount of light is passed through such part.

The distance that the light passes through the finger 18 may be set to about 1 to 2 mm, when for example a wavelength of 1600 nm, i.e., an absorption wavelength of glucose, is to be used. When the distance is over 3 mm, the absorption amount by water increases. Additionally, the angle of the roughly letter V shape to be formed by the recessed part 15 (the angle formed by the first slope part and the second slope part) may be set to 90 degrees to 120 degrees.

With the optical measurement device of this embodiment, in addition to attaining the same effects with the above Embodiment 1, a large amount of the light that passed through the dermis 18b of the finger 18 can be detected by the photodetector 17. Additionally, by disposing the light intensity-reducing part 19 having also a function of a spacer between the light-emitting prism 13 and the light-receiving prism 14 in the optical element 12 to change the distance between the light-emitting prism 13 and the light-receiving prism 14 for optimizing the measurement depth by individuals, the amount of light that passes through a specific portion in the finger 18 is increased, and the signal intensity based on the light can be increased in the photodetector 17. Thus, in the optical measurement device of this embodiment, the S/N ratio of the light to be detected increases, and a highly precise measurement of the concentration of a component can be realized.

Embodiment 3

Figure 5:
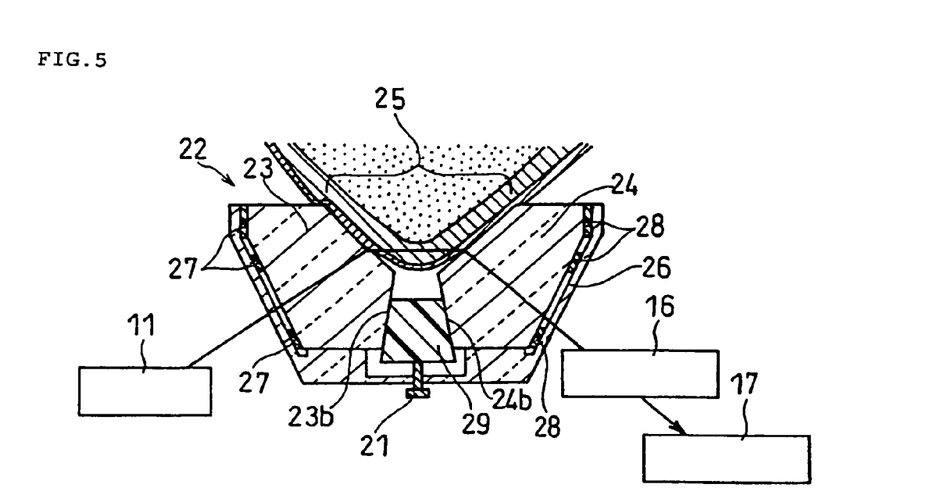
[FIG. 5] A diagram showing a structure of an optical measurement device in Embodiment 3 of the present invention.

FIG. 5 is a diagram showing a structure of an optical measurement device (a measurement device for a concentration of a component) in Embodiment 3 of the present invention using an optical element of the present invention (measurement element). The arrow in the diagram shows a light path. The optical element is described first in the following. In the optical measurement device of Embodiment 3, description for common parts with Embodiment 2 is omitted.

A light intensity-reducing part 29 in this embodiment also has a function of a spacer. In a light-emitting prism 23 and a light-receiving prism 24, the portions lower than a recessed part 25 and facing the light intensity-reducing part 29 to be mentioned later are formed with slope parts 23b and 24b which are planar and with which the distance between the light-emitting prism 23 and the light-receiving prism 24 increases downwardly. The light intensity-reducing part 29 having a trapezoidal cross section perpendicular to the slope parts 23b and 24b is disposed between light-emitting prism 23 and the light-receiving prism 24 while being in contact with the slope parts 23b and 24b.

At a side face and a bottom face of the light-emitting prism 23 and the light-receiving prism 24, adjusting means for adjusting the distance between the light-emitting prism 23 and the light-receiving prism 24 is provided.

The adjusting means is formed with a screw 21 as a movement element for moving the light intensity-reducing part 29 in downward and upward directions, a retaining part 26 for retaining the screw 21, and deforming elements 27 and 28 that are deformable provided in the gap between the retaining part 26 and the light-emitting prism 23, and between the retaining part 26 and the light-receiving prism 24.

The screw 21 is disposed below the light intensity-reducing part 29, and by pushing the light intensity-reducing part 29 from the bottom with the screw 21, the light intensity-reducing part 29 is pressed in upwardly. At this time, when the degree of pressing in is small, the distance between the light-emitting prism 23 and the light-receiving prism 24 can be set short, and when the degree of pressing in is large, the distance between the light-emitting prism 23 and the light-receiving prism 24 can be set long. The deforming elements 27 and 28 elastically absorb the amount of displacement due to the movement of the light-emitting prism 23 and the light-receiving prism 24.

After the movement, although not shown, the light-emitting prism 23 and the light-receiving prism 24 are preferably fixed by fastening with screws from side faces, so that the light-emitting prism 23 and the light-receiving prism 24 do not move again. An adhesive may be used for the fixation.

Although the screw 21 was used for the movement element in this embodiment, the movement element is not limited thereto.

For the deforming elements 27 and 28, for example, a material with elasticity or a spring member may be used. For the material with elasticity, for example, acrylic rubber, urethane rubber, silicone rubber, fluorine rubber, styrene butadiene rubber, butadiene rubber, isoprene rubber, nitrile rubber, chloroprene rubber, or butyl rubber may be used, though not particularly limited.

For the material forming the retaining part 26, plastics or metals are preferable, though not particularly limited. For the metal, for example, aluminum or stainless steel is preferable.

Embodiment 4

Figure 6:
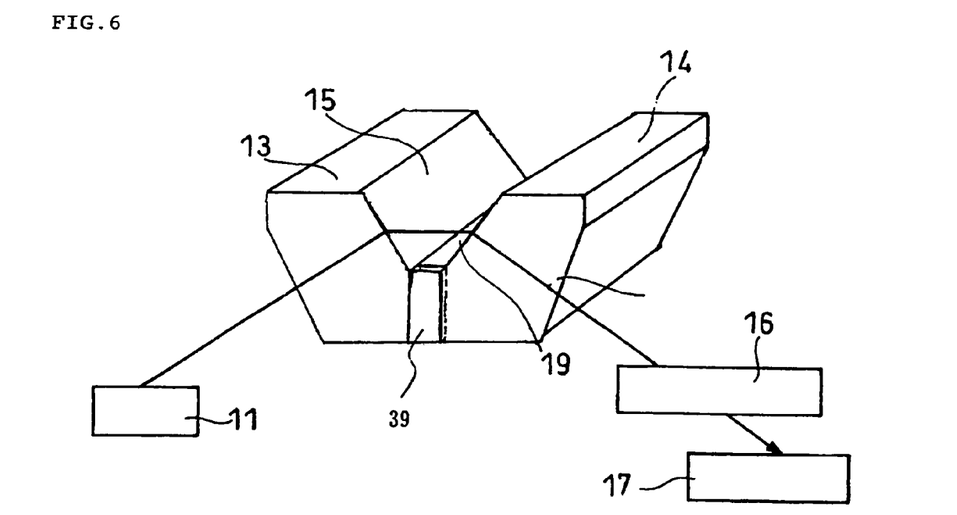
[FIG. 6] A diagram showing a structure of an optical measurement device in Embodiment 4 of the present invention.

FIG. 6 is a diagram showing a structure of an optical measurement device (a measurement device for a concentration of a component) in Embodiment 4 of the present invention using an optical element of the present invention (measurement element). The arrow in the diagram shows a light path. The optical element is described first in the following. In the optical measurement device of Embodiment 4, description for common parts with Embodiment 1 is omitted.

In an optical measurement device of this embodiment, a light-emitting prism 13 and a light-receiving prism 14 are combined with a spacer 39 interposed therebetween other than the light intensity-reducing part 19 comprising a gap between the light-emitting prism 13 and the light-receiving prism 14, it is the same as Embodiment 1.

In this embodiment, since the refractive index of a light at the gap is smaller than the refractive indexes at light-emitting prism 13 and the light-receiving prism 14, from the light that passed through the light-emitting prism 13, the amount of light that enters the light-receiving prism 14 without passing through the sample can be reduced. The arrival of unnecessary light for the detection can be suppressed, and the decline in measurement precision can be reliably suppressed.

Embodiment 5

Figure 7:
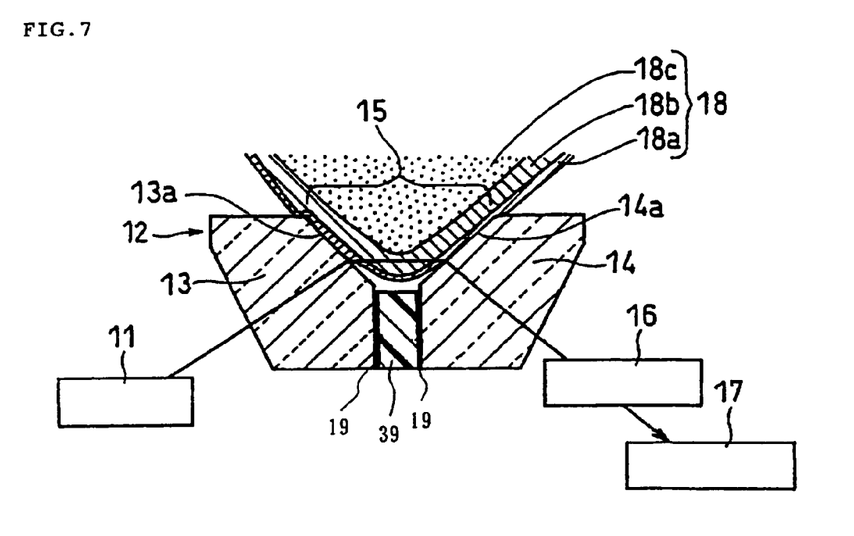
[FIG. 7] A diagram showing a structure of an optical measurement device in Embodiment 5 of the present invention.

FIG. 7 is a diagram showing a structure of an optical measurement device (a measurement device for a concentration of a component) in Embodiment 5 of the present invention using an optical element of the present invention (measurement element). The arrow in the diagram shows a light path. The optical element is described first in the following. In the optical measurement device of Embodiment 5, description for common parts with Embodiment 2 is omitted.

In an optical measurement device of this embodiment, a light-emitting prism 13 and a light-receiving prism 14 are combined with a spacer 39 interposed therebetween. Between the spacer 39 and the light-emitting prism 13, and between the spacer 39 and the light-receiving prism 14, a light intensity-reducing part 19 formed with a film-like light-blocking part is provided.

The spacer 39 has a rectangular shape, and the recessed part 15 is formed by a combination of the light-emitting prism 13, the light-receiving prism 14, the spacer 39, and the light intensity-reducing part 19 to have roughly a shape of letter V. Also, the first slope part 13a which is planar and is in contact with a sample in the light-emitting prism 13, and the second slope part 14a which is planar and is in contact with the sample in the light-receiving prism 14 are disposed to face each other, and are forming side faces of the recessed part 15. The top face of the spacer 19 is positioned at a bottom end of the first slope part 13a and a bottom end of the second slope part 14a to form a bottom face of the recessed part 15.

Thus, by changing the thickness (width) of the spacer 39, a light path of a light that passes through the recessed part 15 can be changed easily. That is, when the spacer 39 is made thicker, the distance between the light-emitting prism 13 and the light-receiving prism 14 increases, a living body goes deeper into the recessed part 15, and a further deeper part of the living body can be measured. Also, when the spacer 19 is made thinner, the distance between the light-emitting prism 13 and the light-receiving prism 14 decreases, and a further frontal layer of the living body can be measured. By thus setting the thickness of the spacer 39 as appropriate, the living body can be measured at a desired depth.

The side faces of the recessed part 15 where the light passes through is formed easily by optically grinding the first slope part 13a and the second slope part 14a to give a smooth face, and joining the light-emitting prism 13 and the light-receiving prism 14 with the spacer 39 interposed therebetween, so that the first slope part 13a and the second slope part 14a face each other. Also, since the first slope part 13a and the second slope part 14a that are planar are optically ground before joining the light-emitting prism 13 and the light-receiving prism 14, the first slope part 13a and the second slope part 14a can be easily smoothed. From the reasons above, the recessed part 15 with high optical precision can be obtained easily.

Although the material for the spacer 39 is not particularly limited, a material which has high mechanical strength, easily absorbs and passes through the light used for the measurement, and is hardly reflective is preferable. For example, glass and plastic are preferable, and by using a material with a smaller refractive index than that of the light-emitting prism 13 and the light-receiving prism 14, the spacer 39 can be provided with a function as a light intensity-reducing part, as described above.

Although the thickness (width) of the spacer 39, that is, the distance between the light-emitting prism 13 and the light-receiving prism 14, is not particularly limited, when a living body is measured for example, since an excessively long optical path length causes an absorption by water to be excessively large, 3 mm or less is preferable.

For the light intensity-reducing part 19, those in the above embodiment may be used.

Although preferred embodiments of the present invention are described in the above, the present invention is not limited thereto, and design change can be made with combinations of various components based on recitations in claims.

For example, although the recessed parts 15 and 25 have roughly a shape of letter V in the above embodiment, the first slope part and the second slope part may have curved face to form a recessed part having roughly a shape of letter U, or the first slope part and the second slope part may have steps to form a recessed part with staircase-like form.

Although a case with a sample of a finger is described in the above embodiment, the sample is not particularly limited thereto. Other than the finger, for example, living body such as lips, lower arms, and ears may be measured as well.

Although a case where a static sample liquid is measured is described in the modified version of Embodiment 1, the present invention is not limited thereto, and a fluid can be measured as well. For example, a component in a fluid can be easily measured as well by connecting a flow path from which a sample liquid flows in with a side face of the first measurement cover 20a, and a flow path from which a sample liquid flows out with a side face of the second measurement cover 20b, thereby making the recessed part 15 a path for a sample liquid to flow, the side face corresponding to the recessed part 15, and the side face corresponding to the recessed part 15.

INDUSTRIAL APPLICABILITY

An optical element and an optical measurement device of the present invention may be suitably used for a measuring device for a concentration of a component, for example, a liquid, a solution, a fluid, and a living body.

The invention claimed is:

1. An optical element comprising:
a light-emitting prism including a light-output face from which a light to be emitted to a sample is outputted;
a light-receiving prism including a light-receiving face which receives the light returned from said sample; and
a light intensity-reducing part provided between said light-emitting prism and said light-receiving prism;
wherein said light intensity-reducing part is a light-blocking part provided between said light-emitting prism and said light-receiving prism;
said light-emitting prism and said light-receiving prism are combined to form a recessed part with which said sample makes contact; and
a light outputted from said light-output face enters said light-receiving face by traveling straight in said sample in contact with said recessed part,
wherein said light-output face of said light-emitting prism is a first slope part which is planar and in contact with said sample;
said light-receiving face of said light-receiving prism is a second slope part which is planar and in contact with said sample; and
said first slope part and said second slope part are facing to form said recessed part, and a cross section of said recessed part in the direction vertical to said first slope part and said second slope part is roughly a shape of the letter V, and
said optical element further comprising a spacer provided between said light-emitting prism and said light-receiving prism.

2. An optical element comprising:
a light-emitting prism including a light-output face from which a light to be emitted to a sample is outputted;
a light-receiving prism including a light-receiving face which receives the light returned from said sample; and
a light intensity-reducing part provided between said light-emitting prism and said light-receiving prism;
wherein said light intensity-reducing part is a light-blocking part provided between said light-emitting prism and said light-receiving prism;
said light-emitting prism and said light-receiving prism are combined to form a recessed part with which said sample makes contact; and
a light outputted from said light-output face enters said light-receiving face by traveling straight in said sample in contact with said recessed part,
wherein said light-output face of said light-emitting prism is a first slope part which is planar and in contact with said sample;
said light-receiving face of said light-receiving prism is a second slope part which is planar and in contact with said sample; and
said first slope part and said second slope part are facing to form said recessed part, and a cross section of said recessed part in the direction vertical to said first slope part and said second slope part is roughly a shape of the letter V, and
said optical element further comprising a cover for covering a part of said recessed part and for forming a sample holding part in combination with said light-emitting prism and said light-receiving prism.

3. An optical element comprising:
a light-emitting prism including a light-output face from which a light to be emitted to a sample is outputted;
a light-receiving prism including a light-receiving face which receives the light returned from said sample; and
a light intensity-reducing part provided between said light-emitting prism and said light-receiving prism;
wherein said light intensity-reducing part is a light-blocking part provided between said light-emitting prism and said light-receiving prism;
said light-emitting prism and said light-receiving prism are combined to form a recessed part with which said sample makes contact; and
a light outputted from said light-output face enters said light-receiving face by traveling straight in said sample in contact with said recessed part;
wherein said light-output face of said light-emitting prism is a first slope part which is planar and in contact with said sample;
said light-receiving face of said light-receiving prism is a second slope part which is planar and in contact with said sample; and
said first slope part and said second slope part are facing to form said recessed part, and a cross section of said recessed part in the direction vertical to said first slope part and said second slope part is roughly a shape of the letter V, and
said optical element further comprising an adjusting means for adjusting a distance between said light-emitting prism and said light-receiving prism.

* * * * *

UNITED STATES PATENT AND TRADEMARK OFFICE
CERTIFICATE OF CORRECTION

PATENT NO. : 7,598,483 B2
APPLICATION NO. : 11/547164
DATED : October 6, 2009
INVENTOR(S) : Shinji Uchida

It is certified that error appears in the above-identified patent and that said Letters Patent is hereby corrected as shown below:

On the title page of the patent, in Item "(56) References Cited," under "Foreign Patent Documents,"

Please delete the reference "JP   60-111946   8/1985"
and add --JP   60-111946   6/1985--.

Signed and Sealed this

Twenty-fifth Day of May, 2010

David J. Kappos
*Director of the United States Patent and Trademark Office*